US010857283B2

(12) United States Patent
Ward et al.

(10) Patent No.: US 10,857,283 B2
(45) Date of Patent: Dec. 8, 2020

(54) WEARABLE HEMOPERFUSION DEVICE

(71) Applicant: EXTHERA MEDICAL CORPORATION, Berkeley, CA (US)

(72) Inventors: Robert S Ward, Orinda, CA (US); Keith R McCrea, Concord, CA (US)

(73) Assignee: EXTHERA MEDICAL CORPORATION, Martinez, CA (US)

( * ) Notice: Subject to any disclaimer, the term of this patent is extended or adjusted under 35 U.S.C. 154(b) by 376 days.

(21) Appl. No.: 14/860,589

(22) Filed: Sep. 21, 2015

(65) Prior Publication Data

US 2016/0082177 A1  Mar. 24, 2016

Related U.S. Application Data

(60) Provisional application No. 62/117,108, filed on Feb. 17, 2015, provisional application No. 62/053,706, filed on Sep. 22, 2014.

(51) Int. Cl.
*A61M 1/36* (2006.01)
*B01D 15/08* (2006.01)
*A61M 1/10* (2006.01)

(52) U.S. Cl.
CPC ........ *A61M 1/3679* (2013.01); *A61M 1/3621* (2013.01); *A61M 1/3659* (2014.02); *B01D 15/08* (2013.01); *A61M 1/101* (2013.01); *A61M 1/1006* (2014.02); *A61M 1/1012* (2014.02); *A61M 2205/12* (2013.01); *A61M 2205/8206* (2013.01); *A61M 2209/088* (2013.01)

(58) Field of Classification Search
CPC .. A61M 1/1006; A61M 1/101; A61M 1/1012; A61M 1/3621; A61M 1/3659; A61M 1/3679; A61M 2205/12; A61M 2205/8206; A61M 2209/088; A61M 1/10; B01D 15/08
See application file for complete search history.

(56) References Cited

U.S. PATENT DOCUMENTS

| 3,782,382 A * | 1/1974 | Naftulin ............... A61M 5/14 |
| | | 604/179 |
| 4,103,685 A | 8/1978 | Lupien et al. |
| 4,415,665 A | 11/1983 | Mosbach et al. |
| 4,430,496 A | 2/1984 | Abbott |
| 4,613,665 A | 9/1986 | Larm |

(Continued)

FOREIGN PATENT DOCUMENTS

| CN | 101370536 A | 2/2009 |
| CN | 101784294 A | 7/2010 |

(Continued)

OTHER PUBLICATIONS

International Search Report; PCT/US2015/051239 dated Dec. 17, 2015.

(Continued)

*Primary Examiner* — John Kim
(74) *Attorney, Agent, or Firm* — Kilpatrick Townsend & Stockton LLP

(57) ABSTRACT

The present technology relates to methods and devices for the removal of toxins and pathogens from infected blood of patients. In particular, devices are designed to be portable, wearable, disposable and self-contained extracorporeal devices that can be easily assembled from a kit.

12 Claims, 7 Drawing Sheets

(56) References Cited

U.S. PATENT DOCUMENTS

| | | |
|---|---|---|
| 4,637,994 A | 1/1987 | Tani et al. |
| 4,820,302 A | 4/1989 | Woodroof |
| 4,955,870 A | 9/1990 | Ridderheim et al. |
| 5,116,962 A | 5/1992 | Stueber et al. |
| 5,211,850 A | 5/1993 | Shettigar et al. |
| 5,403,917 A | 4/1995 | Boos et al. |
| 5,437,861 A | 8/1995 | Okarma et al. |
| 5,447,859 A | 9/1995 | Prussak |
| 5,476,509 A | 12/1995 | Keogh, Jr. et al. |
| 5,753,227 A | 5/1998 | Strahilevitz |
| 6,037,458 A | 3/2000 | Hirai et al. |
| 6,159,377 A | 12/2000 | Davankov et al. |
| 6,197,568 B1 | 3/2001 | Marks et al. |
| 6,248,127 B1 | 6/2001 | Shah et al. |
| 6,312,907 B1 | 11/2001 | Guo et al. |
| 6,461,665 B1 | 10/2002 | Scholander |
| 6,544,727 B1 | 4/2003 | Hei |
| 6,559,290 B1 | 5/2003 | Nakatani et al. |
| 6,653,457 B1 | 11/2003 | Larm et al. |
| 7,179,660 B1 | 2/2007 | Kirakossian |
| 7,408,045 B2 | 8/2008 | Maruyama et al. |
| 7,695,609 B2 | 4/2010 | Soundarrajan et al. |
| 8,663,148 B2 | 3/2014 | Larm et al. |
| 8,758,286 B2 | 6/2014 | Ward et al. |
| 9,173,989 B2 | 11/2015 | Lam et al. |
| 9,408,962 B2 | 8/2016 | Ward et al. |
| 9,669,150 B2 | 6/2017 | Larm et al. |
| 9,764,077 B2 | 9/2017 | Larm et al. |
| 10,086,126 B2 | 10/2018 | Ward et al. |
| 10,188,783 B2 | 1/2019 | Larm et al. |
| 10,457,974 B2 | 10/2019 | Ward et al. |
| 10,487,350 B2 | 11/2019 | Ward et al. |
| 10,537,280 B2 | 1/2020 | McCrea et al. |
| 10,639,413 B2 | 5/2020 | McCrea et al. |
| 10,688,239 B2 | 6/2020 | Larm et al. |
| 2001/0005487 A1 | 6/2001 | Kamibayashi et al. |
| 2002/0018985 A1 | 2/2002 | Eibl et al. |
| 2002/0058032 A1 | 5/2002 | Hirai et al. |
| 2002/0068183 A1 | 6/2002 | Huang et al. |
| 2002/0197249 A1 | 12/2002 | Brady et al. |
| 2002/0197252 A1 | 12/2002 | Brady et al. |
| 2003/0021780 A1 | 1/2003 | Smith et al. |
| 2003/0044769 A1 | 3/2003 | Ogino et al. |
| 2003/0148017 A1 | 8/2003 | Tuominen et al. |
| 2004/0084358 A1 | 5/2004 | O'Mahony et al. |
| 2004/0115278 A1 | 6/2004 | Putz et al. |
| 2004/0140265 A1 | 7/2004 | Lihme |
| 2004/0176672 A1 | 9/2004 | Silver et al. |
| 2004/0182783 A1 | 9/2004 | Walker et al. |
| 2004/0185553 A9 | 9/2004 | Hei |
| 2004/0202783 A1 | 10/2004 | Baumann et al. |
| 2005/0098500 A1 | 5/2005 | Collins et al. |
| 2005/0142542 A1 | 6/2005 | Hei et al. |
| 2005/0244371 A1 | 11/2005 | Lentz |
| 2005/0271653 A1 | 12/2005 | Strahilevitz |
| 2006/0093999 A1 | 5/2006 | Hei |
| 2006/0252054 A1 | 11/2006 | Ping |
| 2007/0190050 A1 | 8/2007 | Davidner et al. |
| 2007/0218514 A1 | 9/2007 | Smith et al. |
| 2007/0231217 A1 | 10/2007 | Clintone et al. |
| 2008/0021365 A1 | 1/2008 | Kobayashi et al. |
| 2008/0138434 A1 | 6/2008 | Brady et al. |
| 2008/0268464 A1 | 10/2008 | Schumacher et al. |
| 2008/0314817 A1 | 12/2008 | Fujita et al. |
| 2009/0105194 A1 | 4/2009 | Flengsrud et al. |
| 2009/0136586 A1 | 5/2009 | Larm et al. |
| 2009/0173685 A1* | 7/2009 | Imai .................. A61M 1/3633 210/243 |
| 2009/0206038 A1 | 8/2009 | Thomas |
| 2009/0246800 A1 | 10/2009 | Mattingly et al. |
| 2009/0325276 A1 | 12/2009 | Battrell et al. |
| 2010/0069816 A1 | 3/2010 | Brady et al. |
| 2010/0079360 A1 | 4/2010 | McLaughlin et al. |
| 2010/0098666 A1 | 4/2010 | Wright |
| 2010/0112725 A1 | 5/2010 | Babu et al. |
| 2010/0145317 A1 | 6/2010 | Laster et al. |
| 2010/0216226 A1 | 8/2010 | Hyde et al. |
| 2010/0217173 A1 | 8/2010 | Hyde et al. |
| 2010/0239673 A1 | 9/2010 | Linhardt |
| 2010/0249689 A1 | 9/2010 | Larm et al. |
| 2010/0276359 A1 | 11/2010 | Ippommatsu et al. |
| 2010/0291588 A1 | 11/2010 | McDevitt |
| 2010/0326916 A1 | 12/2010 | Wrazel et al. |
| 2011/0150911 A1 | 6/2011 | Choo |
| 2011/0171713 A1 | 7/2011 | Bluchel et al. |
| 2011/0184377 A1 | 7/2011 | Ward et al. |
| 2011/0224645 A1 | 9/2011 | Winqvist et al. |
| 2012/0040429 A1 | 2/2012 | Federspiel et al. |
| 2012/0219561 A1 | 8/2012 | Alt et al. |
| 2012/0305482 A1 | 12/2012 | McCrea et al. |
| 2013/0102948 A1 | 4/2013 | Reich et al. |
| 2013/0131423 A1 | 5/2013 | Wang et al. |
| 2014/0012097 A1 | 1/2014 | McCrea et al. |
| 2014/0131276 A1 | 5/2014 | Larm et al. |
| 2014/0231357 A1 | 8/2014 | Ward et al. |
| 2015/0111849 A1 | 4/2015 | McCrea et al. |
| 2015/0260715 A1 | 9/2015 | Hu et al. |
| 2016/0022898 A1 | 1/2016 | Larm et al. |
| 2016/0084835 A1 | 3/2016 | Ward et al. |
| 2016/0101229 A1 | 4/2016 | McCrea et al. |
| 2016/0214935 A1 | 7/2016 | Hutchinson et al. |
| 2016/0331886 A1 | 11/2016 | Ward et al. |
| 2017/0035956 A1 | 2/2017 | McCrea et al. |
| 2017/0073727 A1 | 3/2017 | Ward et al. |
| 2017/0340803 A1 | 11/2017 | Larm et al. |
| 2018/0361050 A1 | 12/2018 | Ward et al. |
| 2019/0038826 A1 | 2/2019 | McCrea et al. |
| 2019/0143027 A1 | 5/2019 | Larm et al. |
| 2020/0023001 A1 | 1/2020 | Ebong et al. |
| 2020/0056221 A1 | 2/2020 | Ward et al. |
| 2020/0171233 A1 | 6/2020 | McCrea et al. |

FOREIGN PATENT DOCUMENTS

| | | |
|---|---|---|
| CN | 102740859 A | 10/2012 |
| DE | 4217917 A1 | 12/1993 |
| EP | 0 306 617 A | 3/1989 |
| EP | 0 321 703 A | 6/1989 |
| EP | 0533946 A1 | 3/1993 |
| EP | 0 616 845 A | 9/1994 |
| EP | 0 810 027 A | 12/1997 |
| EP | 1044696 A2 | 10/2000 |
| EP | 1 057 529 A | 12/2000 |
| EP | 1 110 602 A | 6/2001 |
| EP | 1 219 639 A | 7/2002 |
| EP | 2087916 A1 | 8/2009 |
| EP | 2556849 a1 | 2/2013 |
| GB | 2 172 812 A | 10/1986 |
| JP | 54-127493 U | 9/1979 |
| JP | 58-053757 A1 | 3/1983 |
| JP | 58-146354 A | 8/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 2000-217575 A | 8/2000 |
| JP | 2000-515543 A | 11/2000 |
| JP | 2001-190273 A | 7/2001 |
| JP | 2002-505101 A | 2/2002 |
| JP | 2002-509518 A | 3/2002 |
| JP | 2003-128502 A | 5/2003 |
| JP | 2003-520048 A | 7/2003 |
| JP | 2005-514127 A | 5/2005 |
| JP | 2005-519744 A | 7/2005 |
| JP | 2005-532130 A | 10/2005 |
| JP | 2009-521413 A | 6/2009 |
| JP | 2010-518046 A | 5/2010 |
| JP | 2010-530288 A | 9/2010 |
| JP | 2012-501708 A | 1/2012 |
| JP | 2013-512078 A | 4/2013 |
| JP | 2014-500735 A | 1/2014 |

(56) References Cited

FOREIGN PATENT DOCUMENTS

| | | |
|---|---|---|
| KR | 10-2008-0077405 A | 8/2008 |
| WO | 91/04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/06086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 01/53525 A2 | 7/2001 |
| WO | 02/060512 | 8/2002 |
| WO | 03/033143 A1 | 4/2003 |
| WO | 2003/057356 A2 | 7/2003 |
| WO | 2003/078023 A1 | 9/2003 |
| WO | 2004/008138 A2 | 1/2004 |
| WO | 2004/009798 A2 | 1/2004 |
| WO | 2005/021799 A2 | 3/2005 |
| WO | 2007/058592 A1 | 5/2007 |
| WO | 2007/069983 A1 | 6/2007 |
| WO | 2007/101064 A2 | 9/2007 |
| WO | 2007/146162 A2 | 12/2007 |
| WO | 2008/095905 A2 | 8/2008 |
| WO | 2008/157570 A2 | 12/2008 |
| WO | 2009/121959 A1 | 10/2009 |
| WO | 2010/029317 A2 | 3/2010 |
| WO | 2011/068897 A1 | 6/2011 |
| WO | 2011/100354 A1 | 8/2011 |
| WO | 2012/051595 A1 | 4/2012 |
| WO | 2012/112724 A1 | 8/2012 |
| WO | 2012/172341 A2 | 12/2012 |
| WO | 2013/188073 A1 | 12/2013 |
| WO | 2014/209782 A1 | 12/2014 |
| WO | 2015/069942 A1 | 5/2015 |
| WO | 2015/164198 A1 | 10/2015 |

OTHER PUBLICATIONS

Abdul-Razzak, K. et al., "Fetal and newborn calf thymus as a source of chromatin proteins: Purification of HMG-1 and HMG-2," Preparative Biochemistry and Biotechnology, 17(1):51-61, 1987.

Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.

Chase, H., "Affinity separations utilising immobilised monoclonal antibodies—a new tool for the biochemical engineer," Chemical Engineering Science, 39(7-8):1099-1125, 1984.

Garg, L. et al., "Isolation and separation of HMG proteins and histones H1 and H5 and core histones by column chromatography on phosphocellulose," Protein Expression and Purification, 14(2):155-159, 1998.

Low, R. et al., "Protein n, a primosomal DNA replication protein of *Escherichia coli*," Journal of Biological Chemistry, 257(11):6242-6250, 1982.

Rauvala, H. et al., "Isolation and some characteristics of an adhesive factor of brain that enhances neurite outgrowth in central neurons," Journal of Biological Chemistry, 262(34):16625-16635, 1987.

Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6,1):2293-2305, 1988.

Salmivirta, M. et al., "Neurite growth-promoting protein (Amphoterin, p30) binds syndecan," Experimental Cell Research, 200:444-451, 1992.

Sato, T. et al., "Experimental study of extracorporeal perfusion for septic shock," Asaio Journal, 39(3):M790-M793, 1993.

Wang, H. et al., "HMG-1 as a late mediator of endotoxin lethality in mice," Science, 285:248-251, 1999.

Bindslev et al., "Treatment of acute respiratory failure by extracorporeal carbon dioxide elimination performed with a surface heparinized artificial lung," Anesthesiology, 67(1):117-120, 1987.

Bjorklund et al., Abstract of "Synthesis of silica-based heparin-affinity adsorbents," J. Chrom. A., 728(1-2):149-169, 1996.

Chen et al., "Microbial subversion of heparin sulfate proteoglycans," Mol. Cells, 26:415-426, 2008.

Dixon et al., "Anthrax," New England Journal of Medicine, 341(11):815-826, 1999.

Dubreuil et al., "Effect of heparin binding on Helicobacter pylori resistance to serum," J. Med. Micro., 53:9-12, 2004.

Fujita, M. et al., "Adsorption of inflammatory cytokines using a heparin-coated extracorporeal circuit," Artificial Organs, 26(12):1020-1025, 2002.

Haase et al., "The effect of three different miniaturized blood purification devices on plasma cytokine concentration in an ex vivo model of endotoxinemia," Int. J. Artif. Organs, 31(8):722-729, 2008.

Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectinsl2/Hirmo/paper.htm>.

International Preliminary Report on Patentability, dated Aug. 21, 2013, PCT Application No. PCT/US2012/025316; 8 pages.

International Search Report; PCT/SE2006/001421 dated Mar. 30, 2007.

International Search Report; PCT/US2010/058596 dated Mar. 29, 2011.

International Search Report; PCT/US2011/024229 dated May 30, 2011.

International Search Report; PCT/US2012/025316 dated May 23, 2012.

International Search Report; PCT/US2013/042377 dated Sep. 9, 2013.

International Search Report; PCT/US2014/043358 dated Dec. 1, 2014.

International Search Report; PCT/US2014/064419 dated Feb. 12, 2015.

International Search Report; PCT/US2015/026340 dated Jul. 28, 2015.

Keuren et al., "Thrombogenecity of polysaccharide-coated surfaces," Biomaterials, 24:1917-1924, 2003.

Kim et al., "Role of the heparin in regulating a transcapillary exchange in far north conditions," Bulletin of the Siberian Branch of the Russian Academy of Medical Sciences, 2(108), 2003.

Larm et al., "A new non-thrombogenic surface prepared by selective covalent binding of heparin via a modified reducing terminal residue," Biomater Med Devices Artif Organs, 112&3):161-173, 1983.

Lopatkin et al., "Efferent methods in medicine, M.," Medicine, pp. 266, 272-273, 276-279, 1989.

Mandal, "Sialic acid binding lectins," Experientia, 46:433-439, 1990.

Mariano et al, "Tailoring high-cut-off membranes and feasible application in sepsis-associated acute renal failure: in vitro studies," Nephrol Dial Transplant, 20:1116-1126, 2005.

Nadkarni et al., Abstract of "Directional immobilization of heparin onto beaded supports," Anal. Biochem., 222(1):59-67, 1994.

Ofek et al., "Mannose binding and epithelial cell adherence of *Escherichia coli*," Infection and Immunity, 22(1):247-254, 1978.

Park, P. et al., "Activation of Syndecan-1 ectodomain shedding by *Staphylococcus aureus* α-toxin and β-toxin," J. Biol. Chem., 279(1):251-258, 2004.

Popova et al., "Acceleration of epithelial cell syndecan-1 shedding by anthrax hemolytic virulence factors," BMC Microbiolgy, 6:8, pp. 1-16, 2006.

(56) References Cited

OTHER PUBLICATIONS

Riesenfeld et al., "Quantitative analysis of N-sulfated, N-acetylated, and unsubstituted glucosamine amino groups in heparin and related polysaccharides," Anal Biochem, 188:383•389, 1990.

Sagnella et al., "Chitosan based surfactant polymers designed to improve blood compatibility on biomaterials," Colloids and Surfaces B: Biointerfaces, 42:147-155, 2005.

Sanchez, J. et al., "Control of contact activation on end-point immobilized heparin: The role of antithrombin and the specific antithrombin-binding sequence," J. Bio. Mat. Res., 29:665-661, 1995.

Sasaki et al., Abstract of "Improved method for the immobilization of heparin," J. Chrom., 400:123-32, 1987.

Schefold et al., "A novel selective extracorporeal intervention in sepsis: immunoadsorption of endotoxin, interleukin 6, and complement-activating product 5A," Shock, 28(4):418-425, 2007.

Sharon, "Bacterial lectins, cell-cell recognition and infectious disease," FEBS letters, 217(2):145-157, 1987.

Swartz, "Recognition and management of anthrax—an update," New England Journal of Medicine, 345(22):1621-1626, 2001.

Thomas et al., "Common oligosaccharide moieties inhibit the adherence of typical and atypical respiratory pathogens," Journal of Microbiology, 53:833-840, 2004.

Ward et al., "Specificity of adsorption in a prototype whole blood affinity therapy device for removal of *Staphylococcus aureus*," Society for Biomaterials, 2013 Annual Meeting and Exposition, Apr. 10, 2013, p. 1.

Weber et al., "Development of specific adsorbents for human tumor necrosis factor-α: influence of antibody immobilization on performance and biocompatibility," Biomacromolecules, 6:1864•1870, 2005.

Weir, D., "Carbohydrates as recognition molecules in infection and immunity," FEMS Microbiology Immunology, 47:331-340, 1989.

Wendel et al., "Coating-techniques to improve the hemocompatibility of artificial devices used for extracorporeal circulation," European Journal of Cardio-thoracic Surgery, 16:342-350, 1999.

Yu, J. et al., "Adhesion of coagulase-negative staphylococci and adsorption of plasma proteins to heparinized polymer surfaces," Biomaterials, Biomaterials, 15(10):805-814, 1994.

Zhou et al., Abstract of "Heparin-agarose aqueous ethanol suspension," J. Mol. Bio., 271(3):12, 1997.

Francy, D. et al., "Comparison of filters for concentrating microbial indicators and pathogens in lake water samples," Applied and Environmental Microbiology, 79(4):1342-52, 2012.

Millen, H. et al., "Glass wool filters for concentrating waterborne viruses and agricultural zoonotic pathogens," J. Vis. Exp., 61:e3930, 2012.

Bhakdi, S. and Tranum-Jensen, J., Alpha-toxin of *Staphylococcus aureus*, Microbiological Reviews, 55(4):733-751, 1991.

International Search Report; PCT/US2016/057121 dated Dec. 30, 2016.

Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.

Axelsson, J. et al., "Cytokines in blood from septic patients interact with surface-immobilized heparin," ASAIO Journal, 56:48-51, 2010.

Celik, T. et al., "Treatment of lyme neuroborreliosis with plasmapheresis," J. Clinical Apheresis, 31:476-478, 2016.

Kenig, M. et al., "Identification of the heparin-binding domain of TNF-alpha and its use for efficient TNF-alpha purification by heparin—Sepharose affinity chromatography," J. Chromatography B, 867:119-125, 2008.

Kishimoto, S. et al., "Human stem cell factor (SCF) is a heparin-binding cytokine," J. Biochem., 145(3):275-278, 2009.

Salek-Ardakani, S. et al., "Heparin and heparan sulfate bind interleukin-10 and modulate its activity," Blood, 96:1879-1888, 2000.

International Search Report; PCT/US2017/058536; dated Jan. 17, 2018.

Alfaro et al., "Interleukin-8 in cancer pathogenesis, treatment and follow-up," Cancer Treat Rev., Nov. 2017, vol. 60:24-31 (abstract only).

Kumari, N. et al., "Role of interleukin-6 in cancer progression and therapeutic resistance," Tumour Biol., Sep. 2016, vol. 37(9), pp. 11553-11572 (abstract only).

Lian, S. et al., "Elevated expression of growth-regulated oncogene-alpha in tumor and stromal cells predicts unfavorable prognosis in pancreatic cancer," Medicine, Jul. 2016, 95(30), pp. 1-8.

Mattsby-Baltzer, I. et al., "Affinity apheresis for treatment of bacteremia caused by *Staphylococcus aureus* and/or methicillin-resistant *S. aureus* (MRSA)," J. Microbiol. Biotechnol., 21(6);659-664, 2011.

Waugh D. and Wilson, C., "The interleukin-8 pathway in cancer," Clin. Cancer Res., 14(21):6735-41, 2008.

Webb, L. et al., "Binding to heparan sulfate or heparin enhances neutrophil responses to interleukin 8," PNAS USA, 90:7158-62, 1993.

GE Healthcare, "Size exclusion chromatography columns and resins, Selection guide," 2010, retreived online at <<https://cdn.gelifesciences.com/dmm3bwsv3/AssetStream.aspx?mediaformatid=10061&destinationid=10016&assetid=13947>> on Jun. 27, 2019, 10 pages.

Andrade-Gordon, P. et al., "Interaction of heparin with plasminogen activators and plasminogen: effects on the activation of plasminogen," Biochemistry, 25(14):4033-4040, 1986.

Andreasen, P.A. et al., "The plasminogen activation system in tumor growth, invasion, and metastasis," Cellular and Molecular Life Sciences, 57(1):25-40, 2000.

Brat, D. et al., "The role of interleukin-8 and its receptors in gliomagenesis and tumoral angiogenesis," Neuro-oncology, 7(2):122-133, 2005.

Choong, P.F. et al., "Urokinase plasminogen activator system: a multifunctional role in tumor progression and metastasis," Clinical Orthopaedics and Related Research, 415(Suppl):S46-58, 2003.

Ghannoum, M. et al., "Extracorporeal treatment for carbamazepine poisoning: Systematic review and recommendations from the EXTRIP workgroup," Clinical Toxicology, 52:993-1004, 2014.

Lemaire, M. et al., "Treatment of paediatric vancomycin intoxication: a case report and review of the literature," NDT Plus, 3:260-264, 2010.

Murphy, J.W. et al. "Structural and functional basis of CXCL 12 (stromal cell-derived factor-1 a) binding to heparin," Journal of Biological Chemistry, 282(13):10018-10027, 2007.

Smorenburg, S.M. et al., "The complex effects of heparins on cancer progression and metastasis in experimental studies," Pharmacological Reviews, 53(1):93-106, 2001.

Office Action dated Jun. 23, 2020 in Japanese Patent Application No. 2017-515161, with English translation, retrieved from <https://globaldossier.uspto.gov/#/details/JP/2017515161/A/129021> on Aug. 13, 2020.

Era, K. et al., "Development of Systems for Passive and Active CAVH," J. Japanese Society for Dialysis Therapy, 19(2):175-181, 1986.

Sanaka, T. et al., "Continuous Arteriovenous Hemofiltration," Artificial Organs, 14(5):1822-1830, 1985.

\* cited by examiner

WEARABLE HEMOPERFUSION DEVICE

CROSS-REFERENCE TO RELATED APPLICATIONS

This application claims the benefit of priority to U.S. Provisional Patent Application No. 62/117,108, filed Feb. 17, 2015 and to U.S. Provisional Application No. 62/053,706, filed Sep. 22, 2014, the teachings of which are hereby incorporated by reference in their entireties for all purposes.

BACKGROUND OF THE INVENTION

With urgent threats of drug resistant organisms, untreatable viral outbreaks, and both known and unknown biological weapons, new countermeasures are required for domestic and military use. While significant research is being performed to develop new antibiotics and vaccines, less effort is being invested in other potential countermeasures, such as broad-spectrum extracorporeal therapies.

A device that can safely remove a very broad spectrum of pathogens and toxins can be used for many different types of threats. Additional advantages include rapid performance, reduced risk of side-effects and associated toxicity. However, a potential disadvantage of extracorporeal technologies is device portability, mass scale storage, and a requirement of significant technical training to deploy or respond to a mass casualty event. While drugs may not suffer from these limitations, the process of drug discovery and approval is very slow, and the drug industry simply cannot respond quickly enough to severe outbreaks if a drug is unavailable.

There is a need in the art for an effective self-contained, wearable extracorporeal device that can remove toxins and pathogens from the bloodstream of exposed or infected patients. The devices and methods of the present invention meet this need and provide additional advantageous as well.

BRIEF SUMMARY OF THE INVENTION

In one embodiment, the present invention provides a portable and/or wearable device for extracorporeal removal of a toxin and/or pathogen from blood of an individual infected with a toxin and/or pathogen. The portable and/or wearable device includes a cartridge, the cartridge comprising an adsorption media, wherein the adsorption media is a solid substrate of high surface area having at least one polysaccharide adsorbent on the surface thereof with a binding affinity or binding site for the toxin and/or pathogen such that when the flowing blood is in contact with the adsorption media, the toxin and/or pathogen bind to the binding sites on the at least one polysaccharide adsorbent and become separated from blood. In some embodiments, the device includes a pump such as a rotary pump. In other aspects, the portable and/or wearable device also includes a power source, and optionally an electronic control module. In some aspects, the power source is detachable. The electronic control module can optionally be detachable.

In another embodiment, the present invention provides a portable and/or wearable extracorporeal hemoperfusion device, the device comprising:
  a cartridge comprising adsorption media, the cartridge having a first endplate and a second endplate;
  a blood influx port to allow blood to flow into the device; and
  a blood efflux port to allow blood to flow out of the device, wherein the blood flows through the first endplate through the adsorption media and out the blood efflux port.

In yet another embodiment, the present invention provides an ex vivo method of reducing and/or removing a toxin and/or pathogen in the blood of an individual infected with the toxin and/or pathogen. The extracorporeal method comprises: a) passing blood from the individual through a portable or wearable device comprising an adsorption media, wherein the adsorption media and toxins and/or pathogens in the blood form an adhering complex; b) separating the resulting blood from the adhering complex to produce blood with a reduced level of the toxin and/or pathogen; and c) infusing or returning the blood with the reduced level of the toxin and/or pathogen (back) into the individual.

In some aspects, the blood is selected from the group consisting of whole blood, serum and plasma. In preferred aspects, the blood is whole blood. In some aspects, the adsorption media is a solid substrate of high surface area having at least one polysaccharide adsorbent. In some instances, the at least one polysaccharide adsorbent is selected from the group consisting of heparin, heparan sulfate, hyaluronic acid, sialic acid, carbohydrates with mannose sequences, chitosan, and a combination thereof. The solid substrate can include a plurality of rigid polymer bead. The rigid polymer bead can be selected from the group consisting of polyurethane, polymethylmethacrylate, polyethylene or co-polymers of ethylene and other monomers, polyethylene imine, polypropylene, and polyisobutylene. Alternatively, the solid substrate can include one or a plurality of hollow fibers. In some aspects, the device used in the method also includes a pump.

In some aspects, the portable and/or wearable device is a blood bag.

In some aspects, by performing the method described herein the toxin or pathogen in the blood is reduced by about 10% to about 100%, e.g., about 10%, about 15%, about 20%, about 25%, about 30%, about 35% about 40%, about 45%, about 50%, about 55%, about 60%, about 65%, about 70%, about 75%, about 80%, about 85%, about 90%, about 95% or about 100%. In some aspects, the pathogen in the blood is reduced by about 10% to about 100%, e.g., about 10%, about 15%, about 20%, about 25%, about 30%, about 35% about 40%, about 45%, about 50%, about 55%, about 60%, about 65%, about 70%, about 75%, about 80%, about 85%, about 90%, about 95% or about 100%.

In some aspects, the toxin is selected from the group consisting of *Clostridium botulinum* toxin, ricin toxin from *Ricinus communis*, epsilon toxin of *Clostridium perfringens*, Shiga toxin, and a combination thereof. In some aspects, the pathogen is selected from the group consisting of Ebola virus, Marburg virus, Lassa virus, Junin virus, Machupo virus, Guanarito virus, Chapare virus, Lugo virus, Dengue virus, Garis virus, Ilesha virus, Rift Valley Fever virus, Kyasanur Forest disease virus, Yellow Fever virus, Seoul virus, Crimean-Congo hemorrhagic fever virus, Scandinavian nephropathia epidemica virus, hantavirus, smallpox virus, *Bacillus anthracis, Yersinia pestis*, and *Francisella tularenis*, and a combination thereof. In other aspects, the pathogen is Ebola virus, Marburg virus, Lassa virus, Dengue virus, smallpox virus, *Bacillus anthracis, Yersinia pestis, Francisella tularenis*, and a combination thereof.

In some aspects, the least one polysaccharide adsorbent is selected from the group consisting of heparin, heparan sulfate, hyaluronic acid, sialic acid, carbohydrates with mannose sequences, chitosan, and a combination thereof. The solid substrate can include a plurality of rigid polymer bead. The rigid polymer bead can be selected from the group consisting of polyurethane, polymethylmethacrylate, polyethylene or co-polymers of ethylene and other monomers, polyethylene imine, polypropylene, and polyisobutylene. Alternatively, the solid substrate can include one or a plurality of hollow or solid fibers.

Also provided herein is a kit including the portable and/or wearable device described herein and an instruction manual. In some aspects, the kit includes sterile saline. The kit can also include an anti-coagulant agent, e.g., heparin or a pharmaceutically effective therapeutic agent, e.g., an antiviral drug, an antibacterial drug, or anti-toxin drug.

These and other aspects, objects and embodiments will become more apparent when read with the detailed description which follows.

BRIEF DESCRIPTION OF THE DRAWINGS

FIG. 7A illustrates a blood collection through a filter. FIG. 7B shows autologous transfusion of purified blood through an inventive filter.

DETAILED DESCRIPTION OF THE INVENTION

Figure 1:
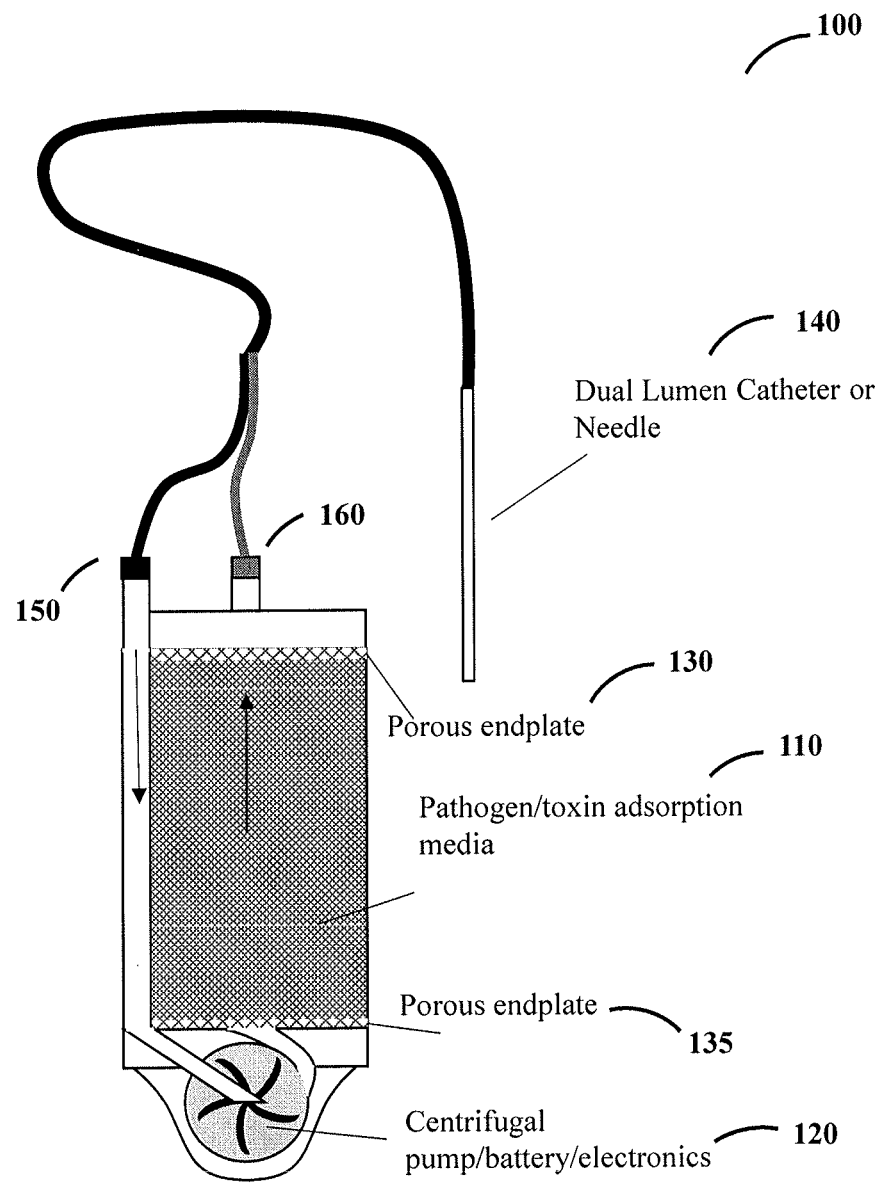
FIG. 1 is a schematic illustration of an exemplary embodiment of an integrated Seraph® pump device with a dual lumen catheter.

The present invention relates in-part to a portable and/or wearable extracorporeal device and methods for removing toxins and/or pathogens from infected or contaminated blood. The methods include using an adsorption media that binds to the toxins and/or pathogens which can be separated from the subject's blood. The toxin- and/or pathogen-free blood can be continuously or intermittently reinfused into the subject.

I. DEFINITIONS

As used herein, the following terms have the meanings ascribed to them unless specified otherwise.

The term "extracorporeal therapy" refers to a medical procedure that is conducted outside the body. In some instances, extracorporeal therapies include methods in which a bodily fluid such as blood is taken from the individual and desired products such as, but not limited to, oxygen, blood-anticoagulants, anesthetics, and the like are added to the body fluid before it is returned to the individual. In other instances, an extracorporeal therapy includes removing undesired products like naturally occurring toxins or poisons from the body or body fluids.

The term "adsorption media" refers to a material to which a cell, organism, virus, toxin, pathogen, polypeptide, polynucleotide, chemical molecule, small molecule, biological molecule or fragment thereof can adhere to the surface thereof.

The term "adhering complex" refers to a complex of at least two molecules wherein the first molecule is attached (e.g., linked, coupled or bound) to the surface of a substrate and the second molecule is attached to the first molecule.

The term "high surface area" refers to the property of having a large specific surface area to volume ratio.

The term "adsorbent" refers to a solid substrate with a chemical compound, a biological molecule, or a material that is attached (e.g., linked, coupled or bound) thereto. In certain instances, the adsorbent is the solid substrate itself. In one embodiment, an adsorbent is a polymer resin with a polysaccharide bound thereto.

The term "rigid polymer bead" refers to a bead, granule, pellet, sphere, particle, microcapsule, sphere, microsphere, nanosphere, microbead, nanobead, microparticle, nanoparticle, and the like that is made from a polymer resin.

The term "carbohydrate" refers to a molecule containing carbon, hydrogen and oxygen atoms, and usually with the empirical formula $C_x(H_2O)_y$, where x and y are different numbers. Examples of carbohydrates includes monosaccharides, disaccharides, oligosaccharides, and polysaccharides.

The term "polysaccharide" refers to a molecule of monosaccharide units joined together by glycosidic bonds, and having an empirical formula of $C_x(H_2O)_y$, where x is between 200 to about 3000.

The term "hydrophilic surface" includes a surface with a water contact angle less than 90° when the surface is flat.

The term "low affinity to heparan sulfate" in the context of a bacteria, refers to the low binding affinity of the bacteria for heparan sulfate. In some aspects, the binding affinity is determined using standard assays, such as an enzyme-linked immunosorbent assay (ELISA) for heparan sulfate. In other aspects, the binding affinity is determined based on a predictive analysis, such as an analysis of putative heparan sulfate binding proteins expressed by the pathogen, e.g., bacteria. The term "no affinity for heparan sulfate" refers to having no binding affinity for, or a lower than detectable affinity for heparan sulfate. In some instances, having no affinity for heparan sulfate includes having no predicted binding affinity for heparan sulfate.

II. DETAILED DESCRIPTIONS OF THE EMBODIMENTS

In one aspect, the wearable hemoperfusion device contains at least one adsorption media optimized for minimal pressure drop, in which arterial pressure is used to move whole blood across the adsorption bed, and returned to venous supply. In certain aspects, a blood pump is placed in series with the adsorption device to provide external pressure for increased blood flow across and/or through the adsorption media. The pump may optionally be integrated into the extracorporeal cartridge to reduce size and weight. Pumps such as centrifugal pumps that are integrated into the cartridge include, but are not limited to, Flow Forward Medical's The Arteriovenous Fistula Eligibility (AFE) System™ or the HeartWare's Circulite® Synergy Pocket Circulatory Assist Device (CAD). If used with veno-venous blood access, inlet flow can be controlled using established methods in order to prevent vein collapse.

A power source and computer control is optionally built into the pump module of the device. In other aspects, a separate, wearable power supply is used, and optionally, reused if connected to a subsequent device. For disposal purposes, a battery or power source and computer module can be ejected from the integrated device prior to disposal or incineration. For cartridges with an integrated rotary pump, the blood supply and return is provided by a dual lumen needle or catheter. Single lumen catheters are also used for arterial supply and venous return, or venous supply and venous return In some aspects, the blood lines are pre-attached to the cartridge containing the adsorption media. The holdup volume of the device can be minimized, and a volume of sterile saline can be included into the integrated device for circuit priming and deairing. Additional safety features include, but are not limited to, a venous return line bubble trap, pressure sensors, and screen filters. Systemic anticoagulation control can also be added and controlled through Venturi liquid injection.

In another embodiment, the present invention provides a portable and/or wearable extracorporeal hemoperfusion device, the device comprising:
a cartridge comprising adsorption media, the cartridge having a first endplate and a second endplate;
a blood influx port to allow blood to flow into the device; and
a blood efflux port to allow blood to flow out of the device, wherein the blood flows through the first endplate through the adsorption media and out the blood efflux port.

With reference to FIG. 1, an embodiment of an extracorporeal hemoperfusion device 100 is described. The device 100 includes a dual lumen catheter or needle 140, a pathogen and toxin adsoption media 110 (e.g., Seraph® Microbind® Affinity Blood Filter; ExThera Medical, Berkeley, Calif.) and porous endplates 130 and 135 at the top and bottom ends of the media, two blood ports 150 and 160 in fluid communication with an optional centrifugal pump 120. The unit that houses the centrifugal pump can also contain a battery and electronics that control the device. The inlet port 150 and the outlet port 160 are in fluid communication with the blood flow path. Typically, the blood enters the device and is contaminated and then leaves the device less contaminated, or decontaminated.

Figure 2:
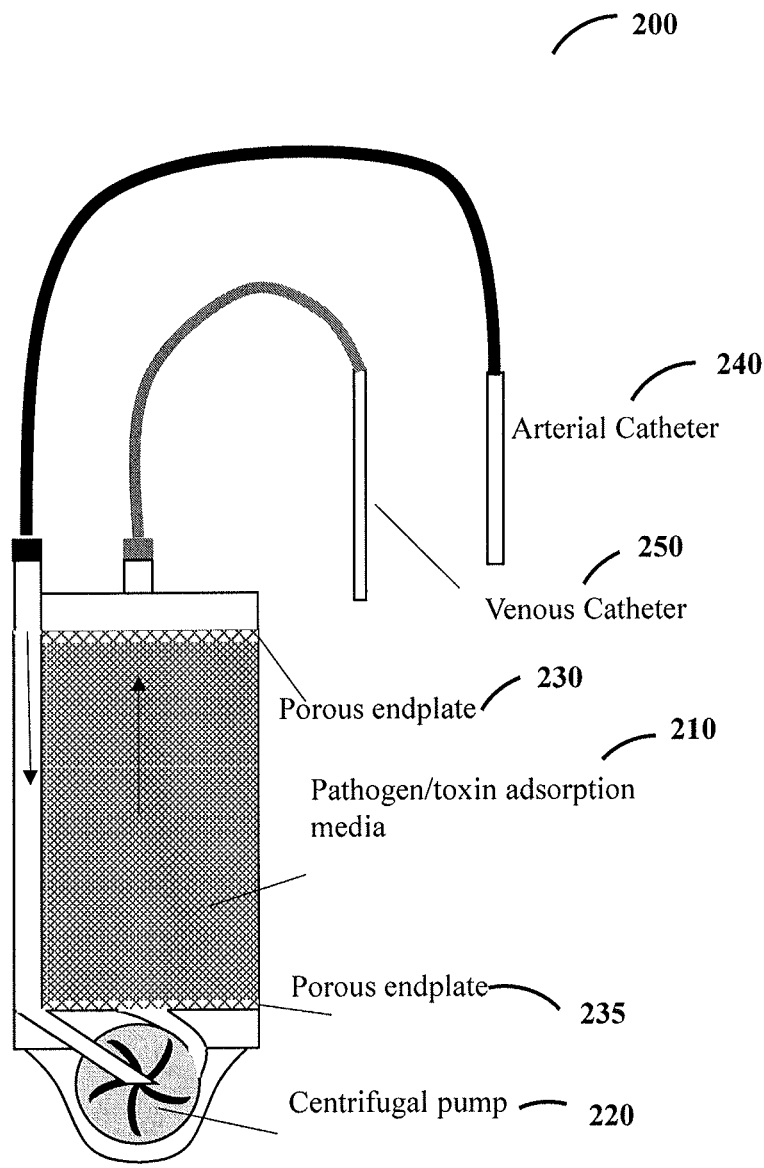
FIG. 2 is a schematic illustration of an exemplary embodiment of an integrated Seraph® pump device with separate arterial (supply) and venous (return) blood access.

Turning now to FIG. 2, an embodiment of an integrated, extracorporeal hemoperfusion device 200 with arterial-venous blood access and a pathogen/toxin adsorption media 210 is shown. The device 200 includes an arterial catheter 240 for the blood to enter the device and a venous catheter 250 for the toxin-free and/or pathogen-free blood to exit the device. Upon entering the device the blood travels to the centrifugal pump 220 and passes through a porous endplate 235 prior to contacting the pathogen/toxin adsorption media 210 of the cartridge. The blood is then pumped through a second porous endplate 230 and flows out through the venous catheter 250 and into the subject. It is comtemplated that the device can be used in the field, e.g., outside a clinical or hospital setting if required.

Figure 3:
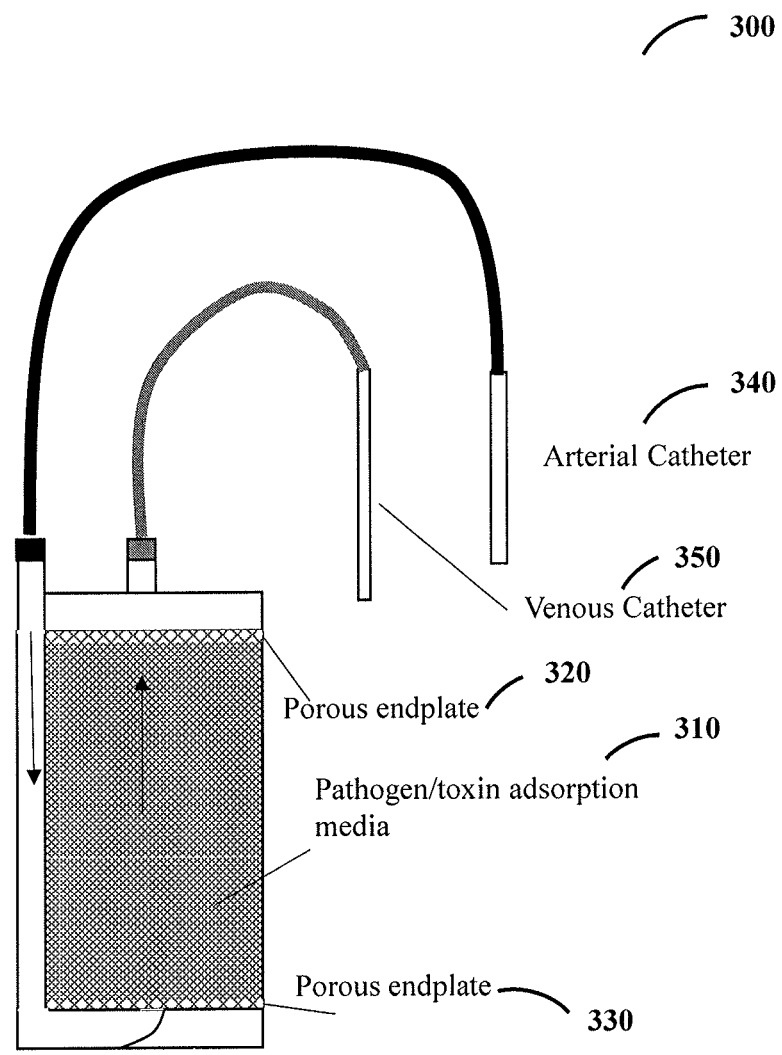
FIG. 3 is a schematic illustration of an exemplary embodiment of a wearable Seraph® pump device with no external pump. The blood flow is driven by differential pressure between arterial and venous pressure.

FIG. 3 illustrates an embodiment of a wearable, extracorporeal hemoperfusion device 300 with no external pump. Blood flow through the device 300 is driven by differential pressure between arterial and venous pressure. The blood enters the device through the arterial catheter 340 and passes to the bottom of the device and then through the porous endplate 330 and into contact with the adsorption media 310. The purified blood flows through a second porous endplate 320 and then the exits the cartridge through the venous catheter 350 to re-enter the subject. In some aspects, such a device has no pump, power source or electronic controls.

Figure 4:
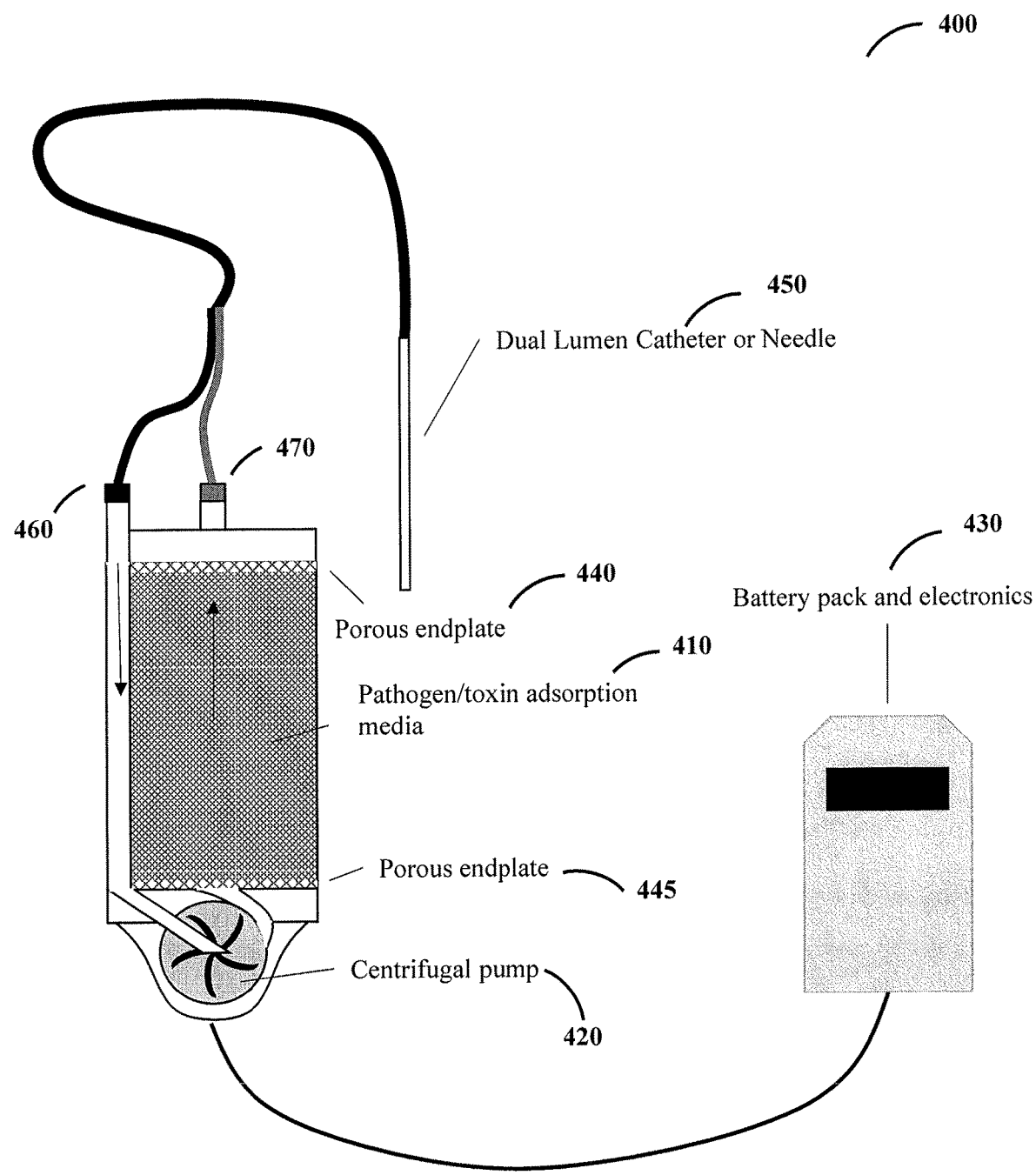
FIG. 4 is a schematic illustration of an exemplary embodiment of an integrated Seraph® pump device with separate arterial and venous blood access. The device has a remote power source and electronic controls.

Next, FIG. 4 provides an embodiment of a wearable, extracorporeal hemoperfusion device 400 with a dual lumen catheter 450 and a remote power source and electronics 430. The device contains a dual lumen catheter or needle 450, a centrifugal pump 420, an adsorption media 410, and an external battery pack and electronics 430. The infected or contaminated blood enters the device 400 through the catheter end and the inlet port 450. The blood passes to the centrifugal pump which is controlled and powered by the remote battery and electronics 430. The blood flows through the porous endplate 445 and comes into contact with the adsorption media 410. The adsorption media removes toxins and pathogens from the blood. The processed blood then passes through the second porous endplate 440 and the outlet port 470. The blood exits the cartridge and flows through the bloodline and re-enters to the subject through the dual lumen catheter or needle 450. The battery pack and electronics module 430 can be detached from the cartridge and pump device and assembled with an unused cartridge and pump device.

Figure 5:
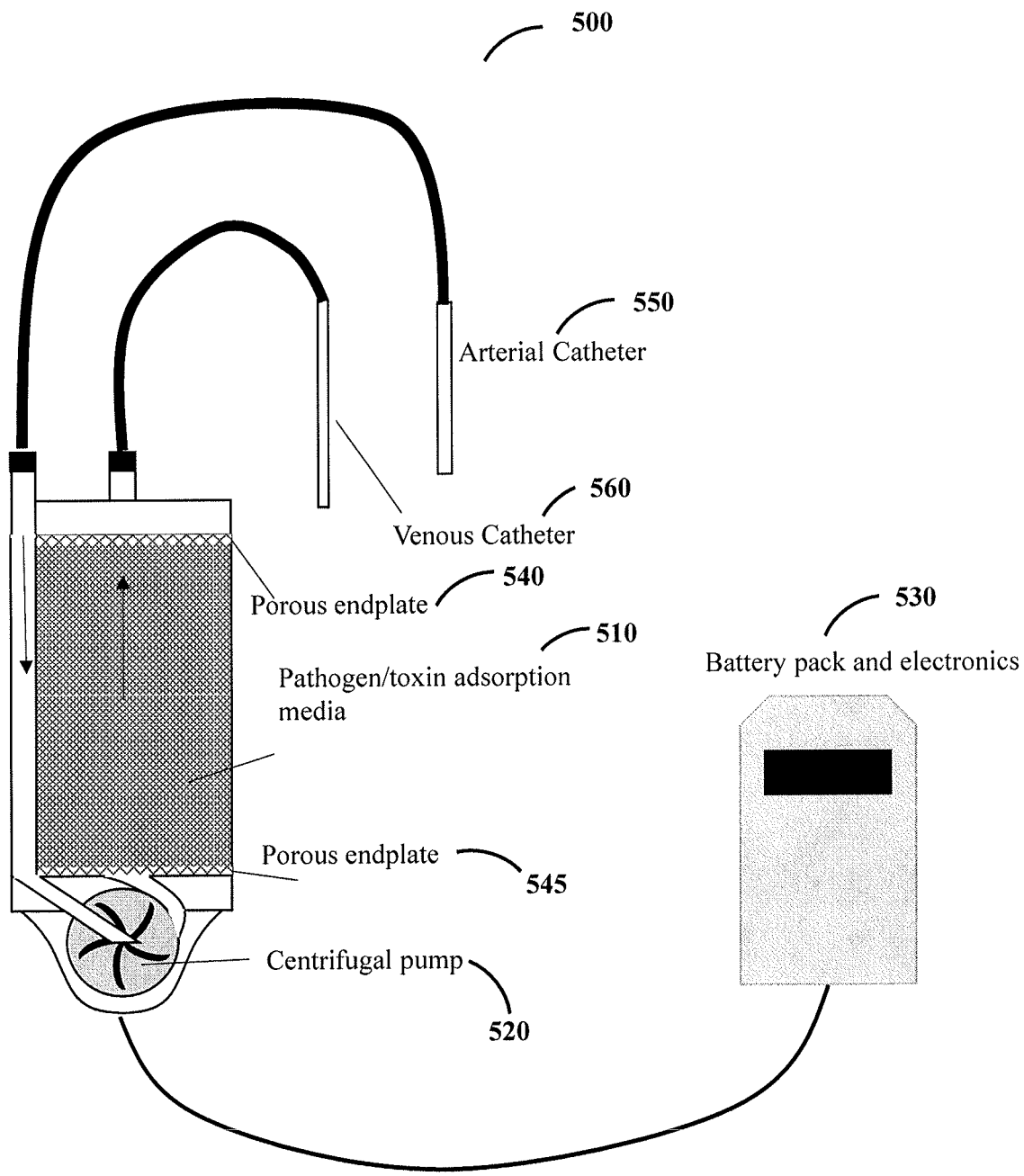
FIG. 5 is a schematic illustration of an exemplary embodiment of an integrated Seraph® pump device w with a dual lumen catheter. The device has a remote power source and electronic controls.

With reference to FIG. 5, an embodiment of an integrated, adsorption and pump device 500 with arterial and venous blood access 550, 560, respectively, and a remote power source and electronics module 530. The device includes an arterial catheter 550, a venous catheter 560, blood lines, a centrifugal pump 520, a pathogen and toxin adsorption media 510, and a external battery pack and electronics 530. The infected or contaminated blood enters through the arterial catheter and passes through the bloodline into the device. The centrifugal pump 520 passes the blood through the porous endplate 545 and into contact with the adsorption media 510. The processed blood flows through the second porous endplate 540 and then an outlet port. The toxin-free and/or pathogen-free blood re-enters the subject through the venous catheter 560. The cartridge containing the adsorption media and the pump is controlled by a battery pack and electronics module 530 that are separate from the adsorption and pump device. The battery pack and electronics module 530 can be detached from the other components of the device and used with other devices.

Figure 6:
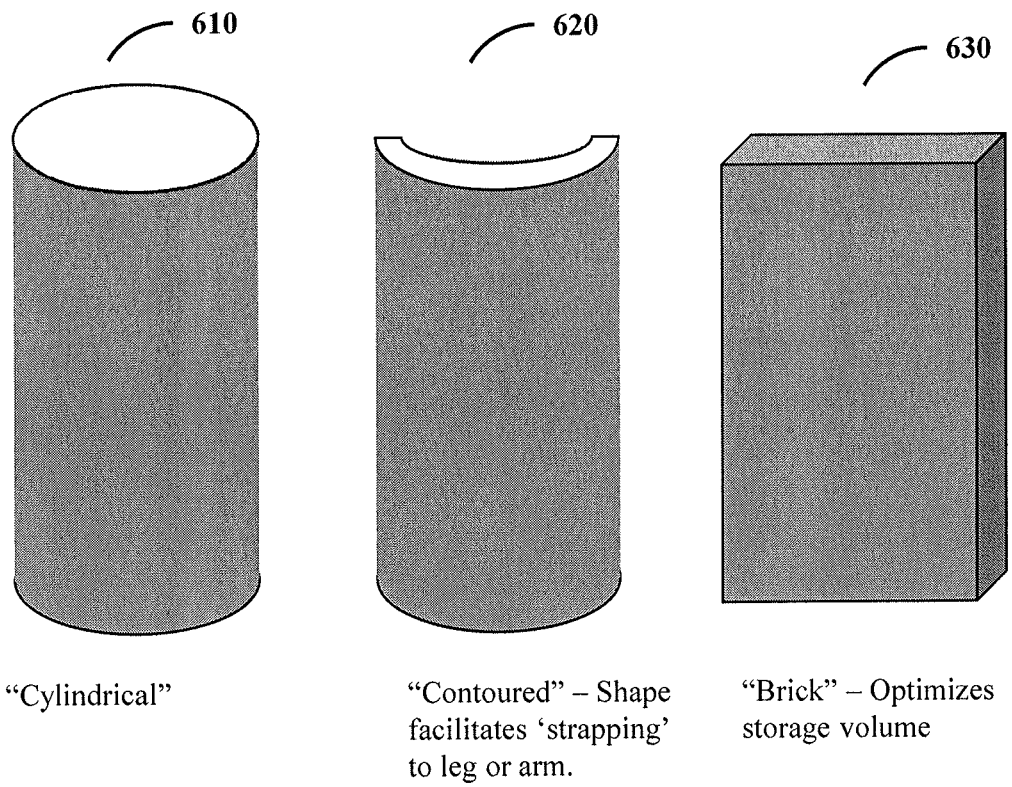
FIG. 6 is a schematic illustration of exemplary embodiments of the filtration cartridge containing the pathogen and toxin adsorption media. The cartridge can be cylindrical 610, contoured 620 or brick-shaped 630.

Turning to FIG. 6, as illustrated therein are several embodiments of the cartridge that are used in the extracorporeal wearable hemoperfusion device described in FIGS. 1-5. The cartridge contains the adsorption media that can remove toxins and pathogens from blood and in some instances, a pump. In some embodiments, the cartridge has a cylindrical shape 610. In other embodiments, the cartridge has a contoured shape that facilitates wearing the device on a leg or arm 620. In yet other aspects, the cartridge has a brick or rectangular block shape which can optimize storage volume 630.

A. Adsorption Media

The adsorption media for small molecule toxins can be a microporous media such as activated carbon or size exclusion chromatography resin that has been rendered blood compatible. Adsorption media for pathogens, such as viruses, bacteria, fungi, or parasites, are preferably coated with at least one affinity ligand such as heparin, heparan sulfate, mannose, dextrose, other carbohydrates, antibodies, and other adhesins, such as opsonins. By including heparin ligands with other non-heparin affinity ligands, the blood compatibility of the device is greatly improved and the broad spectrum characteristics are significantly increased.

The adsorption media is selected according to the use of the device. For instance, a particular media is used to remove a pathogen of interest, including, but not limited to, a virus, e.g., Ebola virus, Marburg virus, Lassa virus, Junin virus, Machupo virus, Guanarito virus, Chapare virus, Lugo virus, Dengue virus, Garis virus, Ilesha virus, Rift Valley Fever virus, Kyasanur Forest disease virus, Yellow Fever virus, Seoul virus, Crimean-Congo hemorrhagic fever virus, Scandinavian nephropathia epidemica virus, hantavirus, and smallpox virus; bacterium, e.g., *Bacillus anthracis, Yersinia pestis*, and *Francisella tularenis*; or toxin, e.g., *Clostridium botulinum* toxin, ricin toxin from *Ricinus communis*, epsilon toxin of *Clostridium perfringens*, and Shiga toxin. Any pathogen or toxin that binds to the adsorption media contained within the disposable adsorption bed or cartridge can be removed by the device provided herein.

Various materials, in shape and composition, can be used as an adsorption media in the present invention. All suitable adsorbent substrates provide high surface area while promoting the conveyance of adsorbates to the adsorbent sites that bind them (primarily) by forced convective or diffusion transport. Useful substrates for creating the adsorption media include non-porous rigid beads, particles, or packing, reticulated foams, a rigid monolithic bed (e.g. formed from sintered beads or particles), a column packed with woven or non-woven fabric, a column packed with a yarn or solid or hollow mesoporous- or microporous-monofilament fibers, a spiral wound cartridge formed from flat film or dense membrane, or a combination of media such as a mixed bead/fabric cartridge. In some embodiments, a suitable substrate for use in the present invention is one that is initially mesoporous or microporous, but becomes essentially non-porous when the surface is treated before, during or after the creation of adsorption sites.

One useful substrate is in the form of solid beads or particles. The beads can be made of materials that are sufficiently rigid to resist deformation or compaction under the encountered flow rates and pressures. In some embodiments, sufficient substrate rigidity is the absence of a significant increase in pressure drop across the adsorption bed during about one hour of flow of water or saline at typical clinical flow rates. For instance, a suitable substrate rigidity is a <10-50% increase in pressure drop relative to the initial pressure drop (e.g., measured within the first minute of flow) when measured at a similar flow rate, e.g., of saline.

The adsorbent substrate beads may be made from a number of different biocompatible materials, such as natural or synthetic polymers or non-polymeric materials including glasses, ceramics and metals, that are essentially free of leachable impurities. Some exemplary polymers including polyurethane, polymethylmethacrylate, polyethylene or co-polymers of ethylene and other monomers, polyethylene imine, polypropylene, and polyisobutylene. Examples of useful substrates include nonporous Ultra High Molecular Weight PolyEthylene (UHMWPE). Other suitable beads are polystyrene, high density and low density polyethylene, silica, polyurethane, and chitosan.

Methods for making such beads are known in the art. For instance, suitable polyethylene beads and other polyolefin beads are produced directly during the synthesis process. In some instances, the beads are processed to the required size and shape. Other polymers may need to be ground or spray dried and classified, or otherwise processed to create beads of the desired size distribution and shape.

In some aspects, the adsorption media of the present invention provides a surface to attach a polysaccharide adsorbent that can bind the bacterial pathogen. In some embodiments, the adsorption media includes a solid substrate with a high surface area having at least one polysaccharide adsorbent on the surface thereof.

In other aspects, the adsorption media of the present invention provides a hydrophilic surface without a polysaccharide adsorbent ("a naked surface"). In some embodiments, the adsorption media includes a solid substrate with a high surface area and a hydrophilic cationic surface. In other embodiments, the adsorption media includes a solid substrate with a high surface area and a hydrophilic neutral surface.

The solid substrate is a material including, but not limited to, polyethylene, polystyrene, polypropylene, polysulfone, polyacrylonitrile, polycarbonate, polyurethane, silica, latex, glass, cellulose, crosslinked agarose, chitin, chitosan, crosslinked dextran, crosslinked alginate, silicone, fluoropolymer, and other synthetic polymers. The solid substrate with a high surface area can be a plurality of adsorbent monolayers, filters, membranes, solid fibers, hollow fibers, particles, or beads. Optionally, the solid substrate can be present in other forms or shapes providing a large surface area.

In certain instances, the solid substrate is a plurality of rigid polymer beads such as polyethylene, polystyrene, polypropylene, polysulfone, polyacrylonitrile, polycarbonate, polyurethane, silica, latex, glass, cellulose, crosslinked agarose, chitin, chitosan, crosslinked dextran, crosslinked alginate, silicone, fluoropolymer, and synthetic polymer beads. Preferably, the rigid polymer beads are polyethylene beads.

The size of the solid substrate can be selected according to the volume of the test sample used in the assay or other parameters. In some embodiments, the each bead of the plurality of rigid polymer beads has an average outer diameter of about 1 µm to about 1 mm, e.g., 1 µm, 2 µm, 3 µm, 4 µm, 5 µm, 6 µm, 7 µm, 8 µm, 9 µm, 10 µm, 15 µm, 20 µm, 25 µm, 30 µm, 35 µm, 45 µm, 55 µm, 60 µm, 65 µm, 70 µm, 75 µm, 80 µm, 85 µm, 90 µm, 95 µm, 100 µm, 200 µm, 300 µm, 400 µm, 500 µm, 600 µm, 700 µm, 800 µm, 900 µm, or 1 mm. In other embodiments, the each bead of the plurality of rigid polymer beads has an average diameter of about 10 µm to about 200 µm, e.g., 10 µm, 15 µm, 20 µm, 25 µm, 30 µm, 35 µm, 45 µm, 55 µm, 60 µm, 65 µm, 70 µm, 75 µm, 80 µm, 85 µm, 90 µm, 95 µm, 100 µm, 105 µm, 110 µm, 115 µm, 120 µm, 125 µm, 130 µm, 135 µm, 140 µm, 145 µm, 150 µm, 155 µm, 160 µm, 165 µm, 170 µm, 175 µm, 180 µm, 185 µm, 190 µm 195 µm, 200 µm or more.

In some embodiments, useful beads have a size ranging from about 100 microns (µm) to 500 µm, or more in diameter, e.g., 100 µm, 150 µm, 200 µm, 250 µm, 300 µm, 350 µm, 400 µm, 450 µm, 500 µm, or more, in diameter. The average size of the beads can be from about 150 µm to about 450 µm in diameter, e.g., 150 µm, 200 µm, 250 µm, 300 µm, 350 µm, 400 µm, or 450 µm in diameter. For example, polyethylene beads from DSM Biomedical (Berkeley, Calif.) having an average diameter of 300 µm are suitable for the present invention.

Beads can be sintered into a monolithic porous structure through either chemical or physical means. Polyethylene beads can be sintered by heating the beads above their melting temperature in a cartridge and applying pressure. The resulting interstitial pore size is slightly reduced from the interstitial pore size of a packed bed of non-sintered beads of equal size. This reduction can be determined empirically and used to produce the desired final interstitial pore size.

Reticulated foams have open cells and can be made from, for example, polyurethanes and polyethylenes. Control of pore size can be achieved by controlling the manufacturing method. In general, reticulated foams can have between 3 and 100 pores/inch and can exhibit a surface area of $\geq 66$ cm$^2$/cm$^3$.

In some embodiments, the substrate is a barrier membrane, e.g., a non-porous film. Alternatively, a microporous membrane may be rendered non-porous by filling the pores with essentially non-porous material, e.g., a polymer. The membrane in the form of a sheet or a solid or hollow fiber may be arranged within a housing or a container.

The adsorption media can be in a vessel such as a column, cartridge, tube, centrifuge tube, and the like, or any vessel wherein the cells of the blood that are not captured onto polysaccharide bound adsorption media can be removed without disturbing the bacterial pathogen attached to the media.

The substrate is typically provided packed within a housing or container, such as a column, that is designed to hold the substrate within the container and permit the blood or serum to flow over the surface of the substrate. The substrate may be arranged within the container to maximize the binding of the adsorbates to the absorbent sides of the substrate. The housing or container may have a macroporous surface structure that provides a large surface area to the blood or serum.

A column or other housing shape can be packed with either woven or non-woven heparinized fabric or the heparin, heparan sulfate or optional non-heparin adsorption sites may be attached, e.g. by covalent, ionic or other chemical or physical bonds, after the housing has been filled with the substrate media. By controlling the fiber denier and density of the fabric during weaving or knitting or during the creation of a non-woven web, the interstitial pore size can be controlled. Useful non-woven fabrics may be in the form of felts, melt-blown, or electrostatically spun webs, having a random orientation held together by entanglement of the fibers and/or adhesion or cohesion of intersecting fibers. Useful woven fabrics have a more defined and non-random structure.

A column can be packed with fibers or yarns made from fibers. Polyethylene, and other fibers can be drawn into thin hollow or solid monofilament fibers or multifilament yarns, which can be packed into cartridges in the same way that hollow fiber membranes are installed within conventional hemodialysis cartridges or blood oxygenators. In the present invention originally porous hollow fibers are rendered dense or non-porous before, during or after binding heparin or other adsorbents to the outer and/or inner surfaces. Dyneema Purity® from Royal DSM is a high-strength solid fiber made of UHMWPE. Dyneema can be heparinized and packed into a cartridge to provide a high-surface area support for the removal of cytokines and pathogens.

A spiral wound cartridge contains a thin film or membrane that is tightly wound together with optional spacer materials to prevent contact of adjacent surfaces. The membrane can be made from polymers such as polyurethane, polyethylene polypropylene, polysulfone, polycarbonate, PET, PBT, and the like.

As noted above, for use in the method of the invention, the size of the channels or interstitial space between individual beads for extracorporeal blood filtration should be optimized to prevent a high-pressure drop between the inlet and outlet of the cartridge, to permit safe passage of the blood cells between the individual beads in a high flow environment, and to provide appropriate interstitial surface area for binding of the polysaccharide adsorbent to the cytokines or pathogens in the blood. For example, in a close packed bed of 300-micron, roughly spherical beads, an appropriate interstitial pore size is approximately 68 microns in diameter.

Various methods of making adsorbents and the adsorbents per se are disclosed in U.S. Pat. No. 8,663,148; U.S. Patent App. Publication Nos. US2009/0136586, US2010/0249689, US2011/0184377, and US2012/0305482, and U.S. Provisional Application Nos. 61/902,070, filed Nov. 8, 2013 and 61/984,013, filed Apr. 24, 2014, the disclosures of which are herein incorporated by reference in their entirety for all purposes.

In some embodiments, the blood-contacting surfaces of the device can be modified for improved or increased blood compatibility. For instances, the surfaces can be modified with optionally endpoint-attached heparin or other active, surface modifers B. Methods of Use The wearable devices and methods provided herein can be used to reduce the level of toxins and/or pathogens in an individual. The method can include obtaining blood from an individual, passing the blood through a cartridge containing an adsorption media, and re-infusing the pass-through blood into the individual. The devices and methods of using thereof can reduce the number of toxins and/or pathogens in the infected or contaminated blood of an individual.

In some embodiments, an anti-coagulation reagent has added to the blood after it enters the device. In other embodiments, a drug therapy, e.g., antiviral therapy can also be administered to the pass-through blood before it re-enters the individual.

The devices can be used in the field, such as in a non-clinical setting. For instance, the device can be worn by an individual outside of a clinic or hospital. In some embodiments, the device is used in a clinical or hospital setting. It can be used as adjunct therapy and used in combination with a drug therapy, such as an antiviral drug.

The devices can be disposable or for single-use. In some instances, the device includes pre-attached blood lines, arterial and/or venous catheters, and a cartridge containing the adsortion media, and optionally a pump such as an integrated rotary pump. An external power source (e.g., battery) and electronics component can be attached to the device. In some embodiments, a kit used to perform the methods provided herein include a wearable, extracorporeal device and an external battery and electronics which can be detached. An instruction manual can be included in the kit.

III. EXAMPLES

The following examples are offered to illustrate, but not to limit, the claimed invention.

Example 1 illustrates the use of a wearable, extracorporeal device that can remove a pathogen from blood of a patient infected or suspected of being infected with the blood-borne pathogen.

The device, as illustrated in FIG. 1, is connected to one of the patient's peripheral arteries via a dual lumen catheter or needle 140. The blood containing or suspected of containing a pathogen such as a virus flows into the device through an inlet port 150 and travels to the cartridge containing the adsorption media 110. A centrifugal or rotorary pump or pulsatile pump 120 that is integrated into the device housing facilitates the movement of the blood pass a first porous endplate 135 and into contact with the adsorption media. The pump is powered by battery 120 and controlled by electronics 120, both of which are housed in the device. The pathogen in the blood becomes immobilized on the surface of the adsorption media by binding to the media and/or one or more polysaccharides attached to the surface of the solid substrate of the media. The blood flow rate is set to optimize the immobilization of the pathogen onto the adsorption media. The constituents of the blood that are not bound to the adsorption media are passed through a second porous endplate 130 and exit the cartridge through an outlet port 160. A bloodline carries the blood containing a reduced level of pathogen back into the patient through the dual lumen catheter or needle 140.

Example 2 illustrates various embodiments of the present invention.

In certain instances, the portable and/or wearable device for extracorporeal affinity comprises an adsorbent media, which quickly and safely removes pathogens and toxins from whole blood in the treatment of a wide range of bloodstream infections. This includes drug-resistant bacteria, viruses and parasites as shown in Table 1. The media does not induce clotting or an inflammatory response in the blood that it contacts, a common problem with other dialysis-like devices that use different binding sites to capture a limited ranges of adsorbates.

The adsorbent media comprises small polyethylene beads with a permanent surface layer of chemically-bonded heparin. Its 'end-point-attached heparin' surface is extremely blood compatible. It mimics the properties of healthy blood vessels which bind 'Antithrombin III' to prevent the blood flowing through them from clotting. Heparin mimics the properties of heparan sulfate (HS) present on the endothelial cells that line veins and arteries, binding the same pathogens and toxins that target HS when invading the bloodstream. This diverts the disease-causing pathogens from the blood onto the surface of a disposable inventive cartridge. After a few hours of treatment, the device reduces the concentration of circulating pathogens to an undetectable level, without generating the toxic byproducts that are released when anti-infective drugs kill circulating pathogens.

TABLE 1

| Drug-Resistant Bacteria | Gram Positive Bacteria | Gram Negative Bacteria | Viruses, Fungi, and Toxins |
|---|---|---|---|
| MRSA | S. aureus | E. Coli | HSV-1, HSV-2, CMV, Adenovirus, Ebola |
| CRE - E. coli and K. pneumoniae | S. pneumoniae | K. pneumoniae | C. albicans |
| ESBL - K. pneumoniae | E. faecalis | Acinetobacter. baumannii | LPS/Endotoxin* |
| VRE - E. faecalis | E. faecium | P. aeruginosa* | S.a. α-hemolysin, Anthrax 'protective antigen' |

Pathogens and toxins already confirmed to bind to the inventive adsorption media are listed in Table 1. The methods and devices herein are effective against Dengue and Malaria (including rosetted red blood cells) and a number of other pathogens and toxins.

In certain instances, the inventive cartridge is used in a dialysis-like therapy during which a dialysis machine continuously circulates blood from the patient through the cartridge and returns it to the patient. A typical treatment time is 4 hours, depending on flow rate and the starting concentration of pathogens in the blood. The current clinical unit is the size of a dialyzer cartridge and contains about 160 grams of the heparin-functional adsorbent 'media'. However, recent quantitative binding studies have shown that this much adsorbent provides up to 600 times more binding capacity than is needed to remove all the bacteria, fungus, or virus present during bloodstream infections.

In certain instances, the binding efficiency is 70 to 99% per pass through the inventive device. This makes it possible to quickly lower the concentration of pathogens in the blood. In MRSA bacteremia, for example, the bloodstream concentration is typically 10 to 1000 CFU/mL, and often less than 100 CFU/mL. One gram of heparin functional adsorption media has enough capacity to bind all the bacteria present in five liters of blood at 100 CFU/mL.

Furthermore, because the adsorption media prevents clotting and presents very low resistance to blood flow, it requires very little pressure differential to operate. In other instances, patients may be treated without dialysis machines.

Several low-cost alternatives to the use of dialysis machines exist and are part of the present invention. These include, for example:
  A small reusable, battery-operated pump optionally integrated into the unit, requiring venous access with a dual-lumen needle;
  Arterial to venous flow (with optional vasopressors) using blood pressure difference to generate flow through an inventive filter; and
  Treatment via a single-needle venous line by using a standard blood bag with adsorbent 'filter' inserted into the blood tubing. (Vasopressors may be required with hypotension, although slow flow during collection is compensated by and more rapid reinfusion.)

Figure 7A:
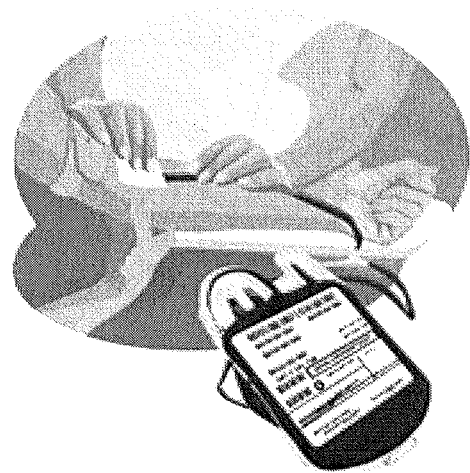
FIGS. 7A-B illustrate an inventive device and treatment without hardware or instrumentation.
Figure 7B:
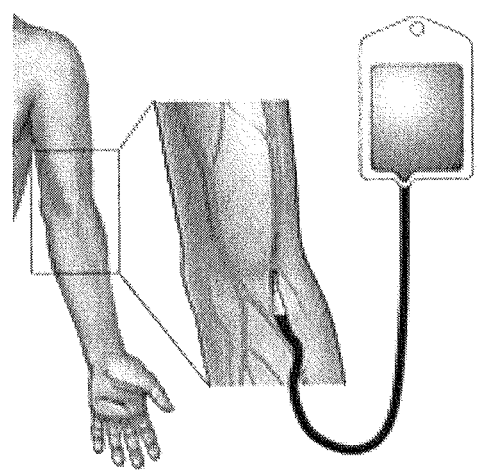

Once the blood bag fills (≥10 min) it is raised above the patient, flowing back through the standard blood bag with adsorbent 'filter' for a second treatment. Since direction of flow does not affect performance, the single unit of blood gets two passes before returning to the patient, affecting a major reduction in pathogen and toxin levels. The process can be repeated several times as needed. Using a low-cost blood bag and needle set eliminates the need for any hardware or instrumentation (an IV pole or even two nails could suffice) and greatly reduces the need for monitoring by healthcare workers. See FIG. 7A-B.

In summary, the cost to implement the present therapy in the treatment of diseases like dengue, malaria and hemorrhagic fevers can be kept very low by downsizing the current (over-sized) filter, and using gravity and/or blood pressure to create flow through the device.

With volume purchasing of heparin and other raw materials, and automated manufacturing of smaller filters, the present invention can be delivered at extremely low cost while benefiting millions of people infected with dengue and malaria.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A portable and/or wearable extracorporeal hemoperfusion device with no pump, the device comprising:
   a blood bag with a directly connected single-needle venous line having a cartridge inserted in-line, which cartridge comprises adsorption media having at least one polysaccharide adsorbent, the cartridge having a first endplate and a second endplate;
   a blood influx port via the single-needle venous line to allow blood to flow into the cartridge;

a blood efflux port to allow blood to flow out of the cartridge, wherein the blood flows from a patient through the first endplate through the adsorption media and out the blood efflux port, and from the blood bag through the blood efflux port, through the cartridge and back into the patient through said single-needle venous line as direction of blood flow through the cartridge does not affect performance; and wherein blood flows through the device is driven by venous pressure and/or gravity as there is no pump.

2. The portable and/or wearable device of claim 1, wherein the least one polysaccharide adsorbent is selected from the group consisting of heparin, heparan sulfate, hyaluronic acid, sialic acid, carbohydrates with mannose sequences, chitosan and a combination thereof.

3. The portable and/or wearable device of claim 1, wherein the adsorption media is a solid substrate, the solid substrate comprising a plurality of rigid polymer beads.

4. The portable and/or wearable device of claim 3, wherein the rigid polymer bead is selected from the group consisting of polyurethane, polymethylmethacrylate, polyethylene or co-polymers of ethylene and other monomers, polyethylene imine, polypropylene, and polyisobutylene.

5. The portable and/or wearable device of claim 3, wherein the solid substrate comprises one or a plurality of hollow fibers.

6. The portable and/or wearable device of claim 1, wherein the device is wearable.

7. The portable and/or wearable device of claim 1, wherein the first endplate is porous.

8. The portable and/or wearable device of claim 1, wherein the second endplate is porous.

9. A ex vivo method of reducing a toxin and/or pathogen in the blood of an individual infected with the toxin and/or pathogen, the method comprising:

passing blood from the individual through a device of claim 1.

10. The method of claim 9, wherein the blood is selected from the group consisting of whole blood, serum and plasma.

11. The method of claim 10, wherein the blood is whole blood.

12. The method of claim 9, wherein the adsorption media is a solid substrate of high surface area having at least one polysaccharide adsorbent.

* * * * *